(12) United States Patent
Marchek et al.

(10) Patent No.: US 9,393,129 B2
(45) Date of Patent: Jul. 19, 2016

(54) BELLOWS-LIKE EXPANDABLE INTERBODY FUSION CAGE

(75) Inventors: Connie Marchek, Foxboro, MA (US); William Frasier, New Bedford, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 456 days.

(21) Appl. No.: 12/635,054

(22) Filed: Dec. 10, 2009

(65) Prior Publication Data

US 2011/0144753 A1 Jun. 16, 2011

(51) Int. Cl.
*A61F 2/44* (2006.01)
*A61F 2/30* (2006.01)

(52) U.S. Cl.
CPC ............ *A61F 2/447* (2013.01); *A61F 2/30742* (2013.01); *A61F 2002/30028* (2013.01); *A61F 2002/30029* (2013.01); *A61F 2002/3055* (2013.01); *A61F 2002/30062* (2013.01); *A61F 2002/3068* (2013.01); *A61F 2002/3093* (2013.01); *A61F 2002/30308* (2013.01); *A61F 2002/30377* (2013.01); *A61F 2002/30462* (2013.01); *A61F 2002/30538* (2013.01); *A61F 2002/30545* (2013.01); *A61F 2002/30556* (2013.01); *A61F 2002/30583* (2013.01); *A61F 2002/30677* (2013.01); *A61F 2002/30904* (2013.01); *A61F 2002/4415* (2013.01); *A61F 2310/00017* (2013.01); *A61F 2310/00023* (2013.01); *A61F 2310/00029* (2013.01)

(58) Field of Classification Search
CPC ........................................................ A61F 2/44
USPC .............................. 623/17.11–17.16; 606/105
See application file for complete search history.

(56) References Cited

U.S. PATENT DOCUMENTS

| 6,049,026 | A | 4/2000 | Muschler |
| 6,127,597 | A | 10/2000 | Beyar et al. |
| 2001/0032020 | A1 | 10/2001 | Besselink |
| 2003/0208203 | A1 | 11/2003 | Lim |
| 2004/0073213 | A1 | 4/2004 | Serhan |
| 2004/0230309 | A1 | 11/2004 | DiMauro |
| 2006/0190083 | A1* | 8/2006 | Arnin ..................... A61F 2/442 623/17.13 |
| 2007/0149978 | A1 | 6/2007 | Shezifi |
| 2007/0233254 | A1 | 10/2007 | Grotz |
| 2007/0282443 | A1* | 12/2007 | Globerman et al. ........ 623/17.11 |
| 2008/0312743 | A1* | 12/2008 | Vila et al. ................... 623/17.16 |
| 2010/0268338 | A1* | 10/2010 | Melkent et al. ............ 623/17.11 |

* cited by examiner

*Primary Examiner* — David Bates
*Assistant Examiner* — Olivia C Chang
(74) *Attorney, Agent, or Firm* — Baker & Hostetler LLP

(57) ABSTRACT

An interbody fusion device having an accordion-like structure, wherein the device in inserted into the disc space in its collapsed configuration and then expanded into its expanded configuration by compressing the accordion-like portion of the device. In some embodiments, a pre-formed tube with an accordion-like structure over a portion of its length is inserted in a relaxed (collapsed) configuration, giving the tube a minimum possible diameter. This tube has a cable running through it that is fixed to a distal end portion of the tube and extends past the proximal end portion of the tube to the outside of the patient. Once the tube is positioned on the rim of the endplate, the proximal end of the cable is pulled, thereby tensioning the cable and causing the accordion portion of the tube to become shorter in length but larger in diameter.

8 Claims, 2 Drawing Sheets

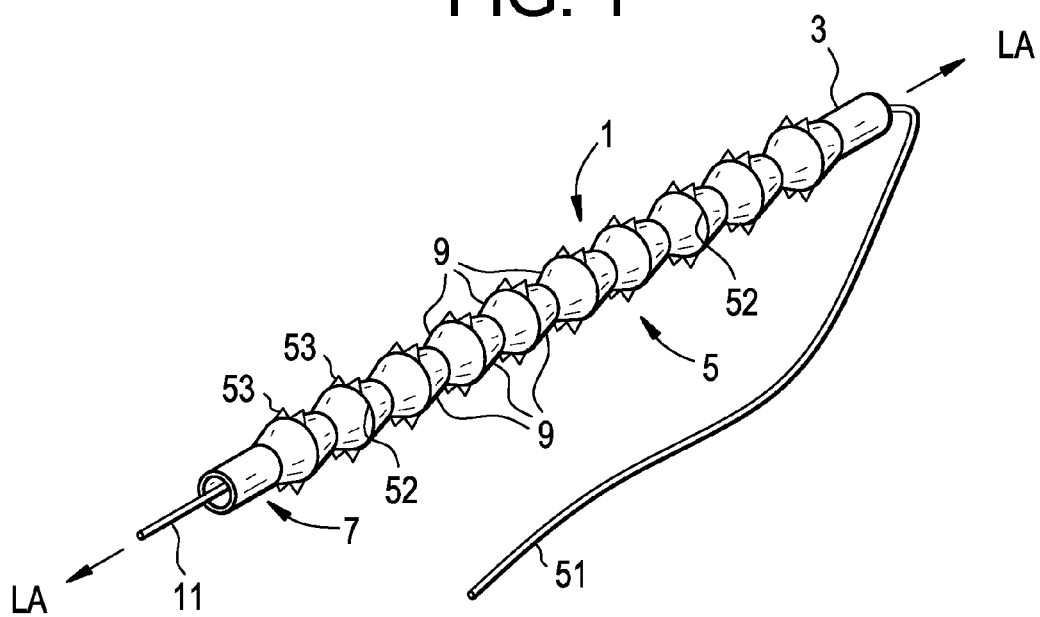
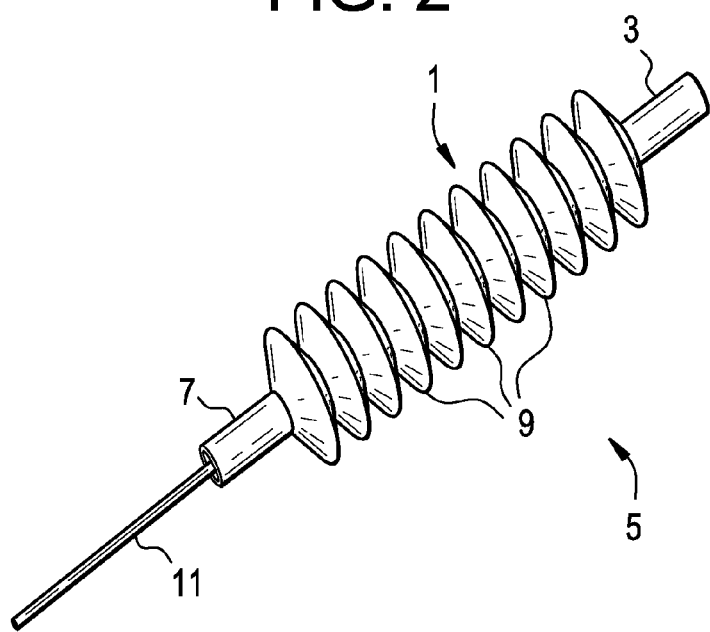

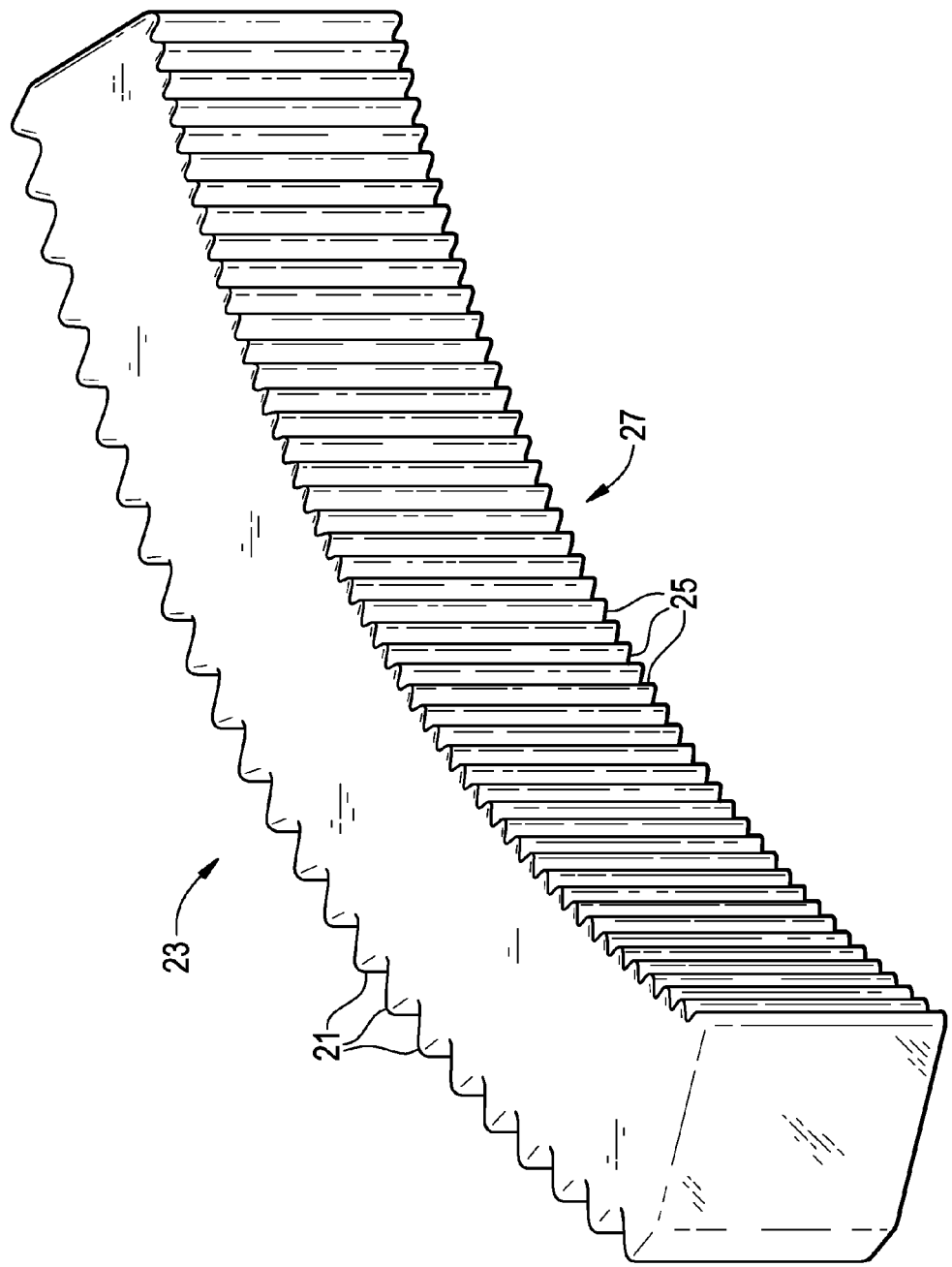

BELLOWS-LIKE EXPANDABLE INTERBODY FUSION CAGE

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices", or "interbody fusion devices".

Current spinal fusion procedures such as transforaminal lumbar interbody fusion (TLIF), posterior lumbar interbody fusion (PLIF), and extreme lateral interbody fusion (XLIF) procedures typically require an 18 mm minimum diameter tube to place an interbody fusion device. Reducing the size of this access portal would help to reduce incision size and muscle trauma due to the procedure. An interbody device that can be inserted through a port that is smaller than the device's final size would help to achieve the goal of reducing incision size, while maintaining proper disc height restoration and providing adequate anterior column support.

US Patent Publication No. 2004-0073213 ("Serhan") is directed toward a device for distracting vertebrae and subsequently delivering a flowable material into the disc space. The distal portion of the device is adapted to distract the vertebrae and the device includes a port for distal delivery of a flowable material.

US Patent Publication No. 2001-0032020 ("Besselink") discloses an expandable intervertebral cage that can accommodate a reinforcing element that itself expands to substantially fill the hollow central portion of the cage.

US Patent Publication No. 2003-0208203 ("Lim") describes a purportedly minimally invasive, articulating insertion instrument for implants, wherein the articulating feature is used to minimize the implant's footprint such that the implant's footprint is transverse to the longitudinal axis of the instrument.

US Patent Publication No. 2004-0230309 ("DePuy Spine") relates to an orthopaedic device for implantation between adjacent vertebrae, the device comprising an arcuate balloon and a hardenable material within the balloon. In some embodiments, the balloon has a footprint that substantially corresponds to a perimeter of a vertebral endplate. An inflatable device is inserted through a cannula into an intervertebral space and oriented so that, upon expansion, a natural angle between vertebrae will at least be partially restored. At least one material component selected from the group consisting of a load-bearing component and an osteobiologic component is directed into the inflatable device through fluid communication means.

US Patent Publication No. 2007-0149978 ("Shezifi") relates to a device for distracting and supporting two substantially opposing tissue surfaces in a minimally invasive procedure. The device comprises a wrapping element and expandable structure insertable between the two substantially opposing support surfaces of the wrapping element and adapted to be expanded between the two substantially opposing surfaces to a predetermined dimension.

US Patent Publication No. 2007-0233254 ("Grotz") is related to expanding spine cages that purportedly expand to conformably engage the endplates of vertebrae by hydraulic means.

Thus, there is a need for additional minimally invasive intervertebral distraction devices and techniques such as those hereinafter disclosed.

SUMMARY OF THE INVENTION

The present invention relates to an interbody fusion device having an accordion—like structure, wherein the device in inserted into the disc space in its radially collapsed configuration and then expanded into its radially expanded configuration by axially compressing the accordion-like portion of the device.

In some embodiments, a pre-formed tube with an accordion-like pleated structure over a intermediate portion of its length is selected as the fusion device of the present invention. This device is inserted in a relaxed (collapsed but elongated) configuration, giving the tube a minimum possible diameter. This tube has a cable running through it that is fixed to a distal end portion of the tube and extends past the proximal end portion of the tube to the outside of the patient. Once the tube is positioned on the rim of the endplate, the proximal end of the cable is pulled, thereby tensioning the cable and causing the accordion portion of the tube to become shorter in length but larger in diameter. The cable is then fixed to the proximal portion of the tube in its tensioned state position (through swaging), and the delivery tube and extraneous cable length are removed. Physiologically, this increase in the outer diameter of the device causes restoration of disc height in the disc space and creates the necessary columnar support.

Therefore, in accordance with the present invention, there is provided an intervertebral fusion device for fusing an intervertebral disc space, comprising:
   a) a tube having a distal end portion, an intermediate portion, a proximal end portion, and a longitudinal axis, the intermediate portion comprising a plurality of pleats arranged substantially perpendicular to the longitudinal axis, and
   b) a first cable disposed within the tube and,
wherein the cable is fixed to the distal end portion of the tube, wherein the tube has a radially collapsed configuration when the first cable is relaxed and a radially expanded configuration when the first cable is tensioned.

Also in accordance with the present invention, there is provided a method of forming an interbody fusion device in a disc space, comprising the steps of:
   i) inserting into the disc space the interbody fusion device of the present invention in its collapsed configuration, and
   ii) tensioning the first cable to place the interbody fusion device in its expanded configuration.

DESCRIPTION OF THE FIGURES

FIG. 1 discloses an intervertebral fusion device of the present invention in its collapsed state.

FIG. 2 discloses an intervertebral fusion device of the present invention in its expanded state.

FIG. 3 discloses an intervertebral fusion device of the present invention wherein the first plurality of pleats associated with the convex outer curve are spaced more widely and are greater in number than the second plurality of pleats associated with the concave inner curve.

DETAILED DESCRIPTION OF THE INVENTION

Now referring to FIGS. 1 and 2, there is provided an intervertebral fusion device for fusing an intervertebral disc space, comprising:
   a) a tube 1 having a distal end portion 3, an intermediate portion 5, a proximal end portion 7, a longitudinal axis LA, and comprising a plurality of pleats 9 arranged substantially perpendicular to the longitudinal axis, and
   b) a first cable 11 disposed within the tube,
wherein the cable is fixed to the distal end portion of the tube, wherein the tube has a radially collapsed configuration (FIG. 1) when the first cable is relaxed and a radially expanded configuration (FIG. 2) when the first cable is tensioned.

In some embodiments, the intermediate portion of the tube bulges when in its expanded configuration. In some embodiments thereof, the pleats are spaced relatively close in the distal and proximal end portions of the tube in its collapsed configuration, and relatively distant in the intermediate portion of the tube in its collapsed configuration, so that, in its expanded configuration, the tube forms large diameter rings in the intermediate portion and small diameter rings in the proximal and distal end portions. This bulging tube is thought to advantageously conform to the contour of the concave surfaces of the opposing endplates that define a disc space. Thus, the folds in this section are designed in such a way that the expanded tube convexly curves to conform to the concave contour of the endplate.

In some embodiments, the inserted tube is caused to curve along its length into a banana shape so that a single device can fully support a disc space. Thus, the banana shape has a concave inner surface and a corresponding convex outer surface.

In some embodiments thereof, and now referring to FIG. 1, the device of the present invention further comprises a second cable 51 disposed outside the tube and fixed to the distal end portion of the tube. Tensioning of this second cable causes the tube to curve.

Now referring to FIG. 3, in some embodiments in which the device has a concave inner curve and a corresponding convex outer curve (such as a banana shape), there is provided a first set of pleats 21 associated with the convex outer curve 23 and a second set of pleats 25 associated with the concave inner curve 27. In this condition, the first set of pleats associated with the convex outer curve are spaced more widely and are greater in number than the second set of pleats associated with the concave inner curve. In such a condition, the bellows is pleated in such a fashion that when it expands the outer curve of the bellows has a larger radius than the inner curve. This may allow the implant to conform to the geometry and curvature of the vertebral endplate.

Therefore, in accordance with the present invention, there is provided an intervertebral fusion device for fusing an intervertebral disc space, comprising:
a banana-shaped tube having a concave inner curve, a corresponding convex outer curve, a distal end portion, an intermediate portion, a proximal end portion, and a longitudinal axis, the intermediate portion comprising a first plurality of pleats 21 associated with the convex outer curve 23 and a second plurality of pleats 25 associated with the concave inner curve 27, wherein the first plurality of pleats associated with the convex outer curve are spaced more widely and are greater in number than the second plurality of pleats associated with the concave inner curve.

In some embodiments, the tube is pleated in such a fashion that, in its expanded configuration, the distal end portion of the tube has a distal radius and the proximal end portion of the tube has a proximal radius, and the distal radius is larger than the proximal radius. This may allow the implant to conform to the geometry and curvature of the vertebral endplate.

In some embodiments, and now referring to FIG. 1, the tube forms a plurality of rings 52 in its expanded configuration, wherein each ring comprises a plurality of teeth 53.

The device may be made of materials typically selected for use in surgical instruments and implants. Preferably, the entire device is sterile.

In some embodiments, the device of the present invention is intended to be permanent. In these cases, the material of construction of pleated tube is a nonresorbable material. In some embodiments thereof, the tube is made from a biocompatible metal (such as a titanium alloy, chrome-cobalt or stainless steel). In others, it is a nonresorbable polymer.

The tube could be filled with hardenable filler, if desired, for additional support. When the tube is made from a nonresorbable material, the filler material is preferably non-resorbable as well.

In some embodiments, the material construction of the tube is a resorbable material. In these embodiments, preferred resorbable materials are PLLA, PGA, and PLGA. When the tube is resorbable, it is desirable for the filler to comprise a bone-forming agent, preferably selected from the group consisting of a porous scaffold, an osteoinductive agent and viable cells.

In other embodiments, the tube may also be filled in accordance with the methods and hardenable materials recited in US Published Patent Application 2004/0230309, filed Feb. 13, 2004 entitled "In-situ formed intervertebral fusion device and method", the specification of which is incorporated by reference in its entirety.

Hardenable, resorbable compositions include setting ceramics, polymerizable monomers and polymers, polymers flowable at temperatures above body temperature, and polymers solubilized in a biocompatible solvent. Examples of resorbable setting ceramics include calcium phosphates, hydroxyapatites and calcium sulfates. Examples of polymerizable resorbable monomers and polymers include polypropylene fumarate), polyoxaesters, polyurethanes and polyanhydrides. In one preferred embodiment, the hardenable composition is a photopolymerized polyanhydride. In this embodiment, irradiation can be used to control the polymerization process, therefore, a partially polymerized putty can be made, then hardened by continuing the polymerization with irradiation after the composition has been placed. Examples of resorbable polymers flowable at temperatures above body temperature include polymers and copolymers of lactic acid, glycolic acid, carbonate, dioxanone, and trimethylene carbonate. An example of a biocompatible solvent that can be used to solubilize the aforementioned polymers include dimethyl sulfoxide.

In order to improve the osteoconductivity of the aforementioned hardenable, resorbable compositions, they may be delivered to the site as an in-situ formed porous scaffold. Techniques of in situ forming porous scaffolds are known in the art and include porogen leaching and foaming with gas-producing elements.

In preferred embodiments of this invention, the hardenable, resorbable compositions incorporate an osteoinductive component. Osteoinductive components include growth factors such as bone morphogenetic proteins that can be grafted onto or mixed into the hardenable compositions. The term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; members of the insulin-like growth factor (IGF) family, including IGF-I and -II; the TGF-β superfamily, including TGF-β1, 2 and 3 (including MP-52); osteoid-inducing factor (OIF), angiogenin(s); endothelins; hepatocyte growth factor and keratinocyte growth factor; members of the bone morphogenetic proteins (BMP's) BMP-1, BMP-3; BMP-2; OP-1; BMP-2A, BMP-2B, and BMP-7, BMP-14; HBGF-1 and HBGF-2; growth differentiation factors (GDF's), members of the hedgehog family of proteins, including indian, sonic and desert hedgehog; ADMP-1; members of the interleukin (IL) family, including IL-1 thru IL-6; GDF-5 and members of the colony-stimulating factor (CSF) family, including CSF-1, G-CSF, and GM-CSF; and isoforms thereof.

In addition, bone-producing cells, such as mesenchymal stem cells (MSCs), can be delivered with the hardenable compositions by first encapsulating the cells in hydrogel spheres then mixing them in. MSCs provide a special advantage because it is believed that they can more readily survive relatively harsh environments; that they have a desirable level of plasticity; and that they have the ability to proliferate and differentiate into the desired cells.

In some embodiments, the mesenchymal stem cells are obtained from bone marrow, preferably autologous bone marrow. In others, the mesenchymal stem cells are obtained from adipose tissue, preferably autologous adipose tissue.

In some embodiments, the mesenchymal stem cells are used in an unconcentrated form. In others, they are provided in a concentrated form. When provided in concentrated form, they can be uncultured. Uncultured, concentrated MSCs can be readily obtained by centrifugation, filtration, or immunoabsorption. When filtration is selected, the methods disclosed in U.S. Pat. No. 6,049,026 ("Muschler"), the specification of which is incorporated by reference in its entirety, are preferably used. In some embodiments, the matrix used to filter and concentrate the MSCs is also administered into the container.

We claim:

1. An intervertebral fusion device for fusing an intervertebral disc space, comprising:
   a) a tube having a distal end portion, an intermediate portion, a proximal end portion, and a longitudinal axis, the intermediate portion comprising a plurality of pleats arranged substantially perpendicular to the longitudinal axis when in a radially collapsed configuration,
   b) a first cable disposed within the tube and,
   c) a second cable disposed outside the tube and fixed to the distal end portion of the tube,
   wherein tensioning of the second cable causes the tube to curve;
   wherein the first cable is fixed to the distal end portion of the tube and runs through the tube so that the first cable extends past the proximal end portion of the tube in a direction of the longitudinal axis,
   wherein the tube has the radially collapsed configuration when the first cable is relaxed and a radially expanded configuration when the first cable is tensioned,
   wherein the second cable is configured to be fixed to the proximal end portion of the tube when the second cable is tensioned,
   wherein the tube forms a plurality of rings in its expanded configuration, wherein at least one ring located in the intermediate portion of the tube comprises a plurality of teeth.

2. The device of claim 1 wherein the first cable is configured to be fixed to the proximal end portion of the tube under tension.

3. The device of claim 1 wherein the tube forms a plurality of rings in its expanded configuration, wherein each ring comprises a plurality of teeth.

4. The device of claim 1 wherein the tube forms a plurality of rings in its expanded configuration, wherein each ring has a diameter substantially equal to a height of the disc space.

5. The device of claim 1 further comprising:
   c) a flowable, hardenable filler material disposed within the tube.

6. The device of claim 5 wherein the filler material is non-resorbable.

7. The device of claim 6 wherein the filler material comprises a bone forming agent.

8. The device of claim 1 wherein the tube is pleated in such a fashion that, in its expanded configuration, the distal end portion of the tube has a distal radius of curvature and the proximal end portion of the tube has a proximal radius of curvature, and the distal radius of curvature is larger than the proximal radius of curvature.

* * * * *